United States Patent
Kelly et al.

(10) Patent No.: US 11,200,974 B2
(45) Date of Patent: Dec. 14, 2021

(54) METHOD AND APPARATUS FOR PROVIDING A QUANTITATIVE VOLUMETRIC MAP OF AN ORGAN OR AN ASSESSMENT OF ORGAN HEALTH

(71) Applicants: Perspectum Limited, Oxford (GB); Matthew Kelly, Oxford (GB); Michael Brady, Oxford (GB); Marija Haramija, Oxford (GB)

(72) Inventors: Matthew Kelly, Oxford (GB); Michael Brady, Oxford (GB); Marija Haramija, Oxford (GB)

(73) Assignee: Perspectum Limited, Oxford (GB)

( * ) Notice: Subject to any disclaimer, the term of this patent is extended or adjusted under 35 U.S.C. 154(b) by 210 days.

(21) Appl. No.: 16/475,885

(22) PCT Filed: Jan. 19, 2018

(86) PCT No.: PCT/EP2018/051321
§ 371 (c)(1),
(2) Date: Jul. 3, 2019

(87) PCT Pub. No.: WO2018/134357
PCT Pub. Date: Jul. 26, 2018

(65) Prior Publication Data
US 2019/0378606 A1   Dec. 12, 2019

(30) Foreign Application Priority Data

Jan. 20, 2017   (GB) .................................. 1701005

(51) Int. Cl.
*G16H 30/00* (2018.01)
*A61B 5/00* (2006.01)
(Continued)

(52) U.S. Cl.
CPC ............. *G16H 30/00* (2018.01); *A61B 5/004* (2013.01); *A61B 5/4244* (2013.01);
(Continued)

(58) Field of Classification Search
None
See application file for complete search history.

(56) References Cited

U.S. PATENT DOCUMENTS 9,993,174 B2 * 6/2018 Rappaport ........... A61B 5/4872
2011/0160546 A1   6/2011 Madsen
(Continued)

FOREIGN PATENT DOCUMENTS

WO    2013088149 A1   6/2013

OTHER PUBLICATIONS

Glombitza Get al: "Virtual planning of liver resections: image processing, visualization and volumetric evaluation", International Journal of Medical Informat, Elsevier Scientific Publishers, Shannon, Ir, vol. 53, No. 2-3, Feb. 1, 1999 (Feb. 1, 1999), pp. 225-237, XP004262423,ISSN: 1386-5056, DOI:10.1016/S1386-5056(98)00162-2figures 3, 6-12Chapters 2.1 Imaging, 2.2 Image transfer, 2.7 Quantitative analysis, 3. Discussion.
Pavlides et. al. Multiparametric magnetic resonance imaging predicts clinical outcomes in patients with chronic liver disease J ournal of Hepatology 2016 vol. 64 j 308 31.

*Primary Examiner* — Tahmina N Ansari
(74) *Attorney, Agent, or Firm* — Optimus Patents US, LLC

(57) ABSTRACT

A method of providing a quantitative volumetric assessment of organ health or a quantitative map of an organ. The method comprises obtaining a volumetric map of organ health comprising information defining a state of tissue health across at least part of an organ, receiving an input defining at least one organ section, determining an assessment organ volume based at least partly on the at least one defined organ section, calculating an organ-viability mea-
(Continued)

sure for the assessment organ volume based at least partly on information within the volumetric map defining the state of tissue health across the organ volume, and outputting an indication of the organ-viability measure.

19 Claims, 6 Drawing Sheets

(51) Int. Cl.
    *G06T 7/00*     (2017.01)
    *A61B 6/00*     (2006.01)
    *G01R 33/50*     (2006.01)

(52) U.S. Cl.
    CPC .......... *A61B 5/7282* (2013.01); *A61B 6/5205* (2013.01); *G01R 33/50* (2013.01); *G06T 7/0012* (2013.01); *G06T 2207/10072* (2013.01); *G06T 2207/30056* (2013.01)

(56) References Cited

U.S. PATENT DOCUMENTS

| | | |
|---|---|---|
| 2012/0321160 A1 | 12/2012 | Carroll |
| 2013/0223714 A1 | 8/2013 | Lipton et al. |
| 2014/0010427 A1* | 1/2014 | Kriston .................. A61B 6/481 382/131 |
| 2014/0330106 A1* | 11/2014 | Banerjee .............. A61B 5/4881 600/410 |
| 2014/0371570 A1 | 12/2014 | Davis |
| 2015/0025372 A1* | 1/2015 | Ghosh .................... A61B 6/032 600/431 |
| 2016/0335770 A1 | 11/2016 | Ming |
| 2017/0083682 A1* | 3/2017 | McNutt ................ A61N 5/1031 |
| 2019/0172270 A1* | 6/2019 | Sudre ...................... G06T 17/10 |
| 2019/0378606 A1* | 12/2019 | Kelly .................. A61B 5/7282 |

* cited by examiner

METHOD AND APPARATUS FOR PROVIDING A QUANTITATIVE VOLUMETRIC MAP OF AN ORGAN OR AN ASSESSMENT OF ORGAN HEALTH

FIELD OF THE INVENTION

This invention relates to a method and apparatus for providing a quantitative volumetric map of an organ or an assessment of organ health. The method may comprise, in particular, a method and apparatus for providing a pre-intervention quantitative volumetric assessment of post-intervention organ health.

BACKGROUND OF THE INVENTION

An MR scanner or a CT scanner may provide very accurate data concerning an organ. However, the raw data from any scanner is rarely suitable for immediate use. There is an ongoing need to convert any available data into accurate but user-friendly information.

The uses of information from medical scans are diverse. Three possible uses for medical information from scans are:

a) Use in a medical study. Medical studies consume vast amounts of medical information, such as that available from longitudinal studies of an organ. The conversion of raw data from an MR or CT image to useable information is the key, for example, to drawing meaningful conclusions in a medical study.

b) Another common use of medical information is by medical practitioners. Practitioners may wish to monitor an organ over time, or may at some point want to make a decision about whether or not to perform an intervention on an organ. Whilst such a decision whether or not to perform an intervention may reside entirely with the medical practitioner, there is a need, prior to the decision, to devise the most accurate and user-friendly information, to offer as a possible input to the medical practitioner's work.

c) In some cases, a medical practitioner may wish to assess the percentage likelihood of death, if a particular medical intervention were to be performed. An assessment that is as precise as possible may aid a medical practitioner to decide which interventions to contemplate, and which have too low a probability of success.

Each of uses a) to c) above is diverse. However, all may wish to rely on accurate information, derived from scan data. Thus, in the field of the present application, there is a clear distinction between the prior derivation of information from data, and then any subsequent use of that information.

Liver resection (removal of all or part of the liver by surgery) is the treatment of choice for curing cancer in the liver, whether due to primary liver cancers such as hepatocellular carcinoma (HCC) or metastatic disease from other sites, for example colorectal cancer (CRC). Advances in surgical technique planning have made curative liver surgery available to increasingly more patients. However, practitioners must have accurate quantitative information, before deciding on and planning any such intervention.

Typically, a surgeon will aim to leave at least one third of the liver volume, i.e. that will remain after the resection. The aim to leave at least one third of the liver volume arises because, in general, one third of a healthy liver is sufficient to support life. However, the rising prevalence of obesity has resulted in an increased proportion of the population having non-alcoholic fatty liver disease (NAFLD) and its more serious subtype, non-alcoholic steatohepatitis (NASH). If a patient undergoing liver resection has a background of liver disease (such as NAFLD or NASH), they will require a larger proportion of liver volume post resection to support life due to the reduced liver function. If too much liver is removed, the patient will require intensive care to compensate for insufficient liver volume. In either case, there is a need for the most precise information possible, based on such data as scans.

The liver is unique in its capacity to withstand surgery and regenerate post-operatively. However, a minimum functional liver remnant (FLR) is required in order for patients to survive the initial peri-operative period. At present, the assessment of the FLR is based solely on volume, in the context of clinical judgment and surrogate markers of liver health (blood tests). There is a clear need for accurate direct measurements, to feed into clinical judgements that may be necessary.

Whilst surgery is the primary approach to curing liver cancer, recent innovations in non-resectional interventions such as Trans-Arterial Chemoembolization (TACE) and radiofrequency ablation (RFA) have demonstrated increasing effectiveness. In fact, TACE is performed more frequently in primary liver cancers than surgery. Since such interventions effectively destroy a portion of the liver, consideration of the FLR is also essential in such non-resectional interventions. Again, there is a need for the most accurate possible information, as an input to any decisions While hepatic steatosis can be determined by non-invasive imaging techniques, steatohepatitis has been shown to be a more important predictor of morbidity. Currently, invasive liver biopsies are frequently performed, in order to provide as much accurate information on which decisions can then be based. In addition to the risks associated with biopsy (pain, bleeding), there is an inherent sampling error with only 0.002% of the liver volume evaluated. Any non-invasive information gathering is preferable to invasive approaches to gaining information.

In addition to the above liver-related issues, partial resections can also be performed on, for example, a patient's pancreas or kidney, which can also suffer from inflammation and fibrosis. Accordingly, measurements of other organs such as kidneys and pancreases may also be beneficial.

Thus, there is a need for a means for providing quantitative volumetric assessments of organs, prior to moving to, for example, surgery. Possible advantages of the invention are a reduction in post-operative intervention and morbidity.

SUMMARY OF THE INVENTION

In accordance with a first aspect of the invention, a method comprising the steps of appended claim 1 is provided. In accordance with a second aspect of the invention, a method comprising the steps of appended claim 18 is provided. In accordance with a third aspect of the invention, an apparatus comprising the features of appended claim 19 is provided. The dependent claims provide further details of embodiments of the invention.

According to example embodiments of a first aspect of the invention there is provided a method of providing a quantitative volumetric assessment of organ health. The method comprises obtaining a volumetric map of organ health comprising information defining a state of tissue health across at least part of an organ, receiving an input defining at least one organ section, determining an assessment organ volume based at least partly on the at least one defined organ section, calculating an organ-viability measure for the assessment organ volume based at least partly on information within the volumetric map defining the state of tissue health across the organ volume, and outputting an indication of the organ-viability measure.

In this manner, a user (e.g. a clinician) is able to provide input to define an assessment organ volume representative of, for example, an anticipated post-intervention organ volume (e.g. an anticipated viable organ volume remaining following resectional surgery or non-resectional interventions). A volumetric map of organ health may then be used to provide a pre-intervention quantitative volumetric assessment of organ health for the anticipated post-intervention organ volume by way of an organ-viability measure. Thus, pre-intervention quantitative information on post-intervention organ health may be provided to, for example, surgeons and interventional radiologists prior to performing any intervention, enabling them to improve surgical/intervention outcomes and to reduce post-surgical/intervention morbidity and cost. In particular, such an assessment is achieved in a non-invasive manner, and enables surgery and/or interventions to be tailored to the individual patient based on the overall health of the patient's organ.

In some optional embodiments, the method may comprise aligning the volumetric map of organ health to a functional organ model (for example, the Couinaud model of hepatic segments), receiving the input from the user defining at least one section of the functional organ model, and determining the assessment organ volume based at least partly on the at least one defined functional organ model section.

In some optional embodiments, the method may further comprise displaying a graphical representation of the functional organ model to the user, and receiving the input from the user defining the at least one organ section in relation to the displayed graphical representation of the function organ model. For example, such a functional organ model may be based on the Couinaud classification of organ anatomy.

In some optional embodiments, the volumetric map of organ health may comprise information defining a state of tissue health for each of a plurality of locations throughout the at least part of the organ, said information comprising at least one of:
  an indication of pathologies present within the respective location of the organ; and
  a health score representative of pathologies present within the respective location of the organ.

In some optional embodiments, the step of calculating the organ-viability measure for the assessment organ volume may comprise calculating an average location health score for all locations within the assessment volume based on information within the volumetric map defining the state of tissue health across the organ volume, and calculating the organ-viability measure for the assessment organ volume based on the average location health score and the assessment organ volume size.

In some optional embodiments, the average location health score for all locations within the assessment volume may comprise identifying pathologies present within each location based on information within the volumetric map defining the state of tissue health across the organ volume, for each location summing weighting values for pathologies identified within that location, and calculating the average location health score based on the summed weighting values for all locations within the assessment volume.

In some optional embodiments, the assessment organ volume may comprise one of:
  the at least one defined organ section; and
  the remaining organ volume excluding the at least one defined organ section.

In some optional embodiments, the method may comprise generating the volumetric map of organ health based on received data indicating the presence of pathologies within locations of at least a part of the organ.

In some optional embodiments, the method may further comprise performing interpolation of the received data indicating the presence of pathologies within locations of the organ to derive indications of the presence of pathologies within locations throughout the whole organ, and generating the volumetric map of organ health based on the derived indications of the presence of pathologies within locations throughout the whole organ.

In some optional embodiments, the step of generating the volumetric map of organ health may comprise identifying pathologies present within individual locations of the organ, for each of said locations summing weighting values for pathologies identified within that location to derive a location health score, and generating the volumetric map of organ health comprising the derived location health scores.

In some optional embodiments, outputting the indication of the organ-viability measure may comprise one or more of:
  displaying the organ-viability measure to a user;
  storing the organ-viability measure in at least one data storage device; and
  transmitting the organ-viability measure to at least one external device.

The at least one organ section may be one of a set of pre-defined functional sections of the organ, based on a segmental anatomy of the organ. The set of pre-defined organ sections may be sections of a Couinaud classification system, for example Couinaud sections of a liver. A selection of at least one pre-defined organ section may be an interactive process, whereby the user is able to select and/or unselect different segments and combinations of segments. A received input may define one or more sections, at least one of the sections being only part of a function section, thereby excluding at least another part of the function section. The input volumetric map of organ health may be a corrected MRI-derived T1, 'cT1', map of the liver.

According to example embodiments of a second aspect of the invention, a method of providing a quantitative volumetric map of an organ comprises obtaining a volumetric map of an organ, the volumetric map comprising information defining a state of tissue across at least part of an organ. The method further comprises receiving an input defining at least one organ section, determining an assessment organ volume based at least partly on the at least one defined organ section, and calculating a measure of the state of the assessment organ volume, based at least partly on information within the input volumetric map defining the state of the tissue across the organ volume. The method then further comprises outputting an indication of the measure of the state of the assessment organ volume.

According to example embodiments of a third aspect of the invention there is provided an apparatus for providing a quantitative volumetric assessment of organ health or a quantitative volumetric map of an organ, the apparatus comprising at least one processing component arranged to perform the method of the first or second aspects of the invention.

In some optional embodiments, the at least one processing component may comprise one or more of:
  one or more programmable components arranged to execute computer program code for performing one or more of the steps of the method of the first or second aspects of the invention; and hardware circuitry arranged to perform one or more of the steps of the method of the first or second aspects of the invention.

In some optional embodiments, the apparatus may further comprise at least one output component for outputting the indication of the organ-viability measure. The at least one output component may comprise one or more of:
- a display device for displaying the organ-viability measure to a user;
- a data storage device for storing the organ-viability measure; and
- an interface component for transmitting the organ-viability measure to at least one external device.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

DETAILED DESCRIPTION OF THE PREFERRED EMBODIMENTS

The present invention will now be described with reference to the accompanying drawings in which there is illustrated an example of a method and apparatus for providing a pre-intervention quantitative volumetric assessment of post-intervention organ health. However, it will be appreciated that the present invention is not limited to the specific examples herein described and as illustrated in the accompanying drawings and that various modifications and alternatives may be implemented without departing from the inventive concept.

Furthermore, because the illustrated embodiments of the present invention may for the most part, be implemented using electronic components and circuits known to those skilled in the art, details will not be explained in any greater detail than that considered necessary as illustrated below, for the understanding and appreciation of the underlying concepts of the present invention and in order not to obfuscate or distract from the teachings of the present invention.

Figure 1:
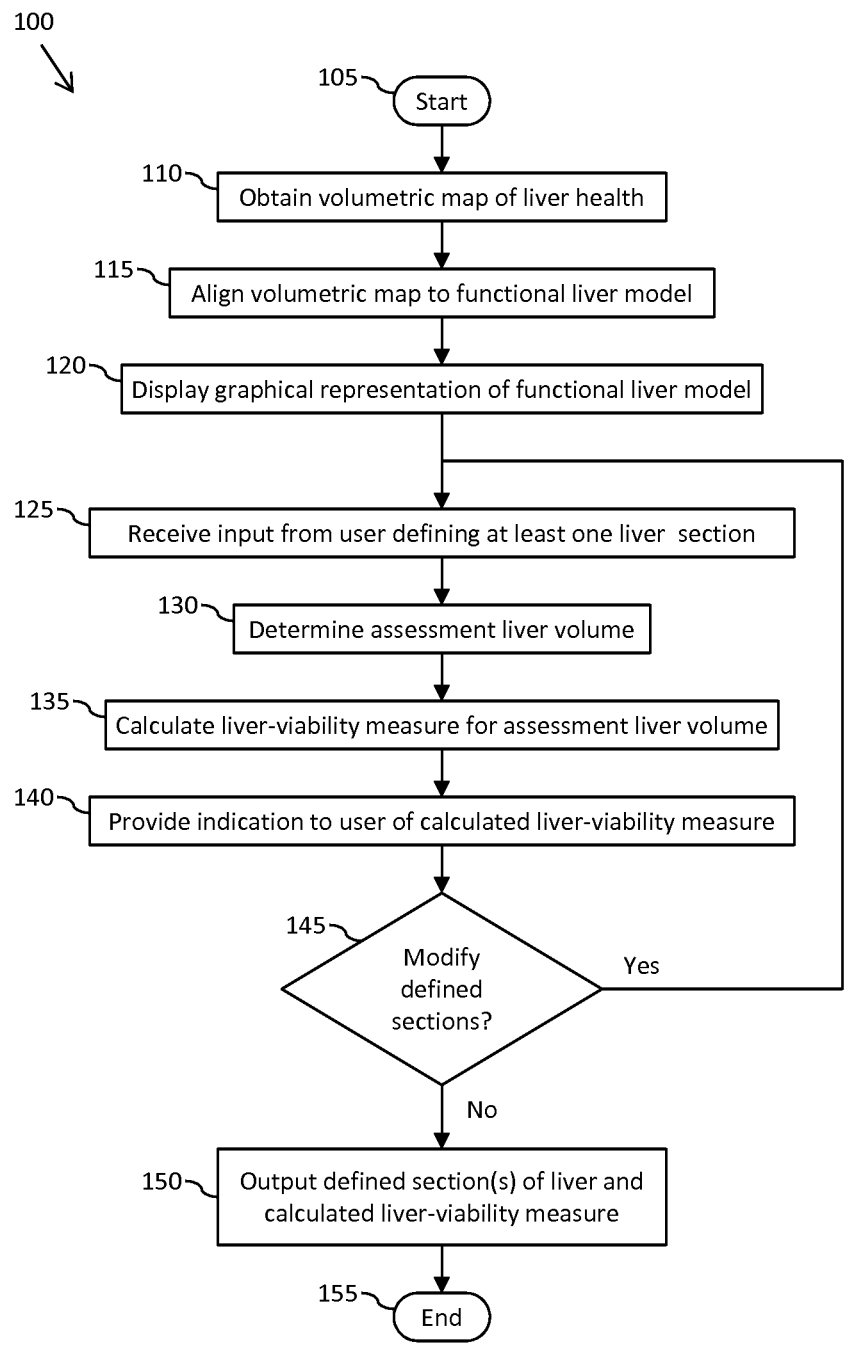
FIG. 1 illustrates a simplified flowchart of an example of a method of providing a quantitative volumetric assessment of organ health for planned/anticipated organ treatment.

Referring now to FIG. 1, there is illustrated a simplified flowchart 100 of an example of a method of providing a quantitative volumetric assessment of post-intervention organ health for planned/anticipated organ treatment. The method of FIG. 1 starts at 105 and moves on to 110 where a volumetric map of organ health for an organ, for example a liver, is obtained. The volumetric map of organ health comprises information defining a state of tissue health across at least part of the organ. For example, the volumetric map of organ health may comprise information defining a state of tissue health for each of a plurality of locations throughout the organ.

In some example embodiments, such information for a location within the organ may comprise an indication of pathologies present within that location of the organ. Examples of pathologies that may be present within, for example, a liver, and thus that may be indicated within the volumetric map information, include:
- steatosis (the abnormal retention of fats and other lipids within a cell);
- inflammation (the increased movement of plasma and white blood cells into the tissue);
- fibrosis (the formation of excess fibrous connective tissue); and
- cirrhosis (scarring of the liver tissue).

Each individual 'location' of the organ may be representative of, for example, a voxel of a medical scan image of the organ, such as an MRI scan, CT scan, fused imaging data set (e.g. PET-CT) etc. As such, each location of the organ may be representative of, for example, a 2 mm$^2$ section of a 2-D medical scan slice through the organ having a certain slice 'thickness', and thus be representative of a volume comprising many cells. Accordingly, multiple pathologies may be present within the region of the organ represented by an individual location for which information is provided within the volumetric map of organ health. Thus, in some example embodiments, the information within the volumetric map of organ health for a location within the organ may comprise an indication of the presence of one or more pathologies, or in the case of a healthy region of organ an indication of the presence of no pathologies.

In some alternative embodiments, the information within the volumetric map of organ health for a location within the organ may comprise a health score representative of pathologies present within the respective location of the organ. For example, and as described in greater detail below with reference to FIG. 5, such a location health score may be derived based on pathologies present within that location, with different pathologies being assigned different weighting values, and the location health score being derived based on the sum of the weighted values for pathologies present within the location. It will be appreciated that alternative approaches to computing a representation of combined information about a plurality of pathologies may equally be used to derive a location health score, and the approaches herein described are only intended to be exemplary and not limiting.

Referring back to FIG. 1, having obtained the volumetric map of the organ health, the method moves on to 115 where in the illustrated example the volumetric map of organ health is aligned to a functional organ model. One example of such a functional liver model is the Couinaud classification of liver anatomy, which uses the vascular supply in the liver to separate the liver into eight functional segments. Such a functional liver model is typical relied upon by surgeons and interventional radiologists for planning and during surgery/intervention to determine the extent of the surgery/intervention. Such alignment may be achieved by way of performing registration, for example deformable registration, between the volumetric map of organ health and the functional organ model to align the data set of the volumetric map of organ health into the volumetric coordinate system of the functional organ model. Image registration is a well-known process within the art, with many different, well-known techniques available for performing such an alignment of datasets. Accordingly, such alignment will not be described in any further detail herein.

By aligning the volumetric map of organ health to such a function organ model, the information within the volumetric map of organ health defining the state of tissue health can be directly linked to the function organ model during planning etc. of organ surgery/intervention.

In the example illustrated in FIG. 1, having aligned the volumetric map of organ health to the functional organ model, the method moves on to 120 where in the example of FIG. 1 a graphical representation of the functional organ model is displayed to a user. In this manner, the user is able to visualise a model of the organ and to interact with the model for the purpose of surgery/intervention planning, including selecting/defining sections of the organ. In the illustrated example, input from the user defining one or more sections of the functional organ model are then received at 125, for example defining one or more organ sections in relation to the displayed graphical representation of the functional organ model. However, it is contemplated that such input defining one or more sections of the organ may alternatively be automatically generated, and thus it will be appreciated that the present invention is not limited to such input being provided by a user. The sections defined by the received input may relate to functional sections of the organ defined by the functional organ model, for example the eight functional segments defined by the Couinaud classification system. Additionally, alternatively one or more sections defined by the received input may relate to a part of such a function section, referred to as a 'wedge' in resection surgery.

An assessment organ volume is then defined 130 based on the received input from the user. For example, such input from the user may define one or more sections to be removed/ablated during surgery/intervention. Accordingly, the assessment organ volume may be determined to comprise those sections of the functional organ model not defined by the received input. Alternatively, the input from the user may define one or more sections of the organ to remain post-surgery/intervention. Accordingly, the assessment organ volume may be determined to comprise those sections defined by the received input.

Having determined the assessment organ volume, the method moves on to 135 where an organ-viability measure for the assessment organ volume is calculated based at least partly on information within the volumetric map of organ health. Example methods of calculating an organ-viability measure for an assessment organ volume are described below with reference to FIGS. 2 and 3.

Having calculated the organ-viability measure for the assessment organ volume, the method moves on to 140 where an indication of the calculated organ-viability measure is provided to a user. Such an indication may be provided in any suitable manner. For example, the organ-viability measure may be displayed to the user as a numeric value, or by way of a graphical representation (e.g. colour/shade) applied to the functional organ model displayed to the user. Additionally, alternatively the organ-viability measure may be compared to one or more threshold value(s) representative of a viable organ assessment volume, and an indication of whether the organ-viability measure is above or below the threshold value(s) may be displayed to the user. Such an indication of whether the organ-viability measure is above or below the threshold value may be represented by way of a numeric value or word, or by a colour applied to the graphical representation of the functional organ model displayed to the user.

In the example illustrated in FIG. 1, the user is provided with an opportunity to modify the defined sections at 145. If the user selects to modify the defined sections, the method loops back to 125 where (further) input from the user one or more (modified) section(s) is received. Conversely, if no modifications to the defined sections are required by the user, the method moves on to 150 where in the illustrated example the defined organ sections and at least an indication of the calculated organ-viability measure are output. Outputting of the indication of the organ-viability measure and the defined organ sections may comprise one or more of:

displaying the organ-viability measure to a user;
storing the organ-viability measure in at least one data storage device; and
transmitting the organ-viability measure to at least one external device.

The method of FIG. 1 then ends, at 155.

Thus FIG. 1 demonstrates a method in accordance with the first aspect of the invention. In accordance with the second aspect of the invention, the method of FIG. 1 also enables a method of providing a quantitative volumetric map of an organ. In this case, step 110 comprises obtaining a volumetric map of an organ, the input volumetric map comprising information defining a state of tissue across at least part of the organ. The method further comprises receiving an input defining at least one organ section, as generally described at step 125. As at step 130, an assessment organ volume is determined, based at least partly on the at least one defined organ section. As at step 135, the method can comprise generally calculating a measure of the state of the assessment organ volume, based at least partly on information within the input volumetric map from step 110 defining the state of the tissue across the organ volume. In the case of the method of the second aspect of the invention, step 150 comprises outputting an indication of the measure of the state of the assessment organ volume. The applicant has provided a separate flowchart to show in detail the steps of the method of the second aspect of the invention, see FIG. 7, which is discussed in greater detail at the end of this detailed description.

The steps and features discussed below in connection with FIGS. 2-6, and the steps of appended dependent claims 2-17, may be employed with either the method of the first aspect of the invention or with the method of the second aspect of the invention. For example, the interpolation step 415 of FIG. 4 may also be employed with the method of the second aspect of the invention. For simplicity, the remaining description builds on the wording used in the method of the first aspect of the invention, i.e. the method of appended independent claim 1 and FIG. 1, rather than the wording of the second aspect of the invention as claimed in appended claim 18 and in FIG. 7, but this choice is not limiting.

Figure 2:
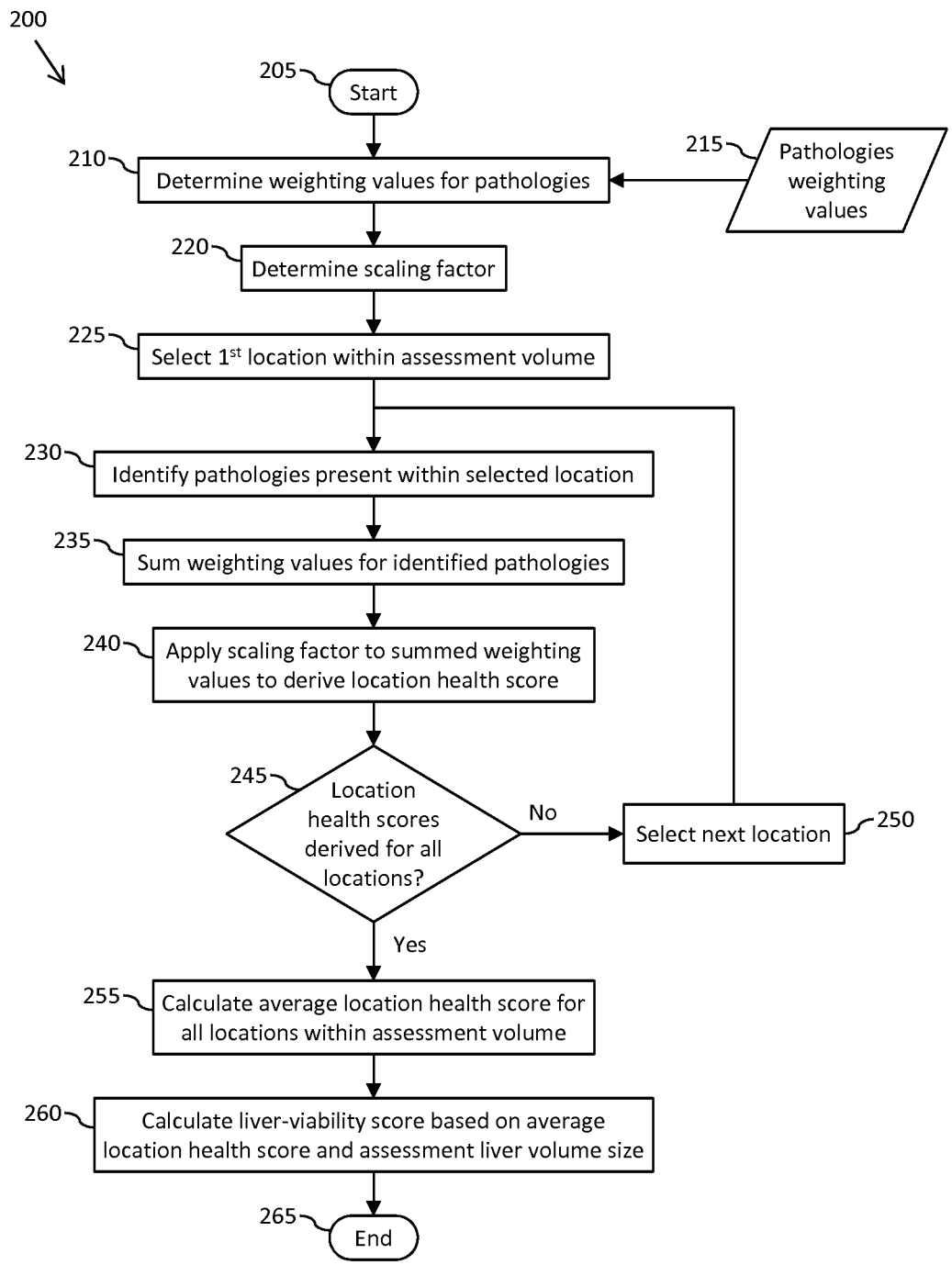
FIG. 2 illustrates a simplified flowchart of an example of a method of calculating an organ-viability measure when the volumetric map of organ health comprises information defining an indication of pathologies present within each location of the organ.

FIG. 2 illustrates a simplified flowchart 200 of an example of a method of calculating an organ-viability measure when the volumetric map of organ health comprises information defining an indication of pathologies present within each location of the organ. The method of FIG. 2 starts at 205 and moves on to 210 where weighting values for pathologies are determined. For example, such pathology weighting values 215 may be predefined and retrieved from a data storage device. Additionally, alternatively, such pathology weighting values 215 may be manually entered by a user. In the illustrated example, a scaling factor for the weighting values is then determined at 220, for example to normalise a subsequently calculated organ-viability score to a pre-defined range (e.g. a range from 0 to 1). Such a scaling factor may be determined by summing the weighting values and dividing a top-end range value (e.g. 1) by the summed value. A first location within the assessment volume is then selected at 225.

Pathologies present within the selected location are identified at 230 based on the information for that location contained within the volumetric map of organ health. The weighted values for the pathologies identified as being present within the selected location are summed at 235. In the illustrated example, the scaling factor determined at 220 is then applied to the summed weighting values at 240 to derive a location health score. It is then determined whether location health scores have been derived for all locations within the assessment volume at 245. If it is determined that location health scores have not been derived for all locations within the assessment volume, the next location is selected at 250 and the method loops back to 230.

When it is determined that location health scores have been derived for all locations within the assessment volume at 245, the method moves on to 255 where an average location health score for all locations within the assessment volume is calculated. The organ-viability score for the assessment volume is then calculated at 260 based on the average location health score and the assessment organ volume size, for example the absolute size of the assessment organ volume or a relative size assessment organ volume (e.g. as a percentage or ratio of the full organ volume). The method then ends at 265.

Figure 3:
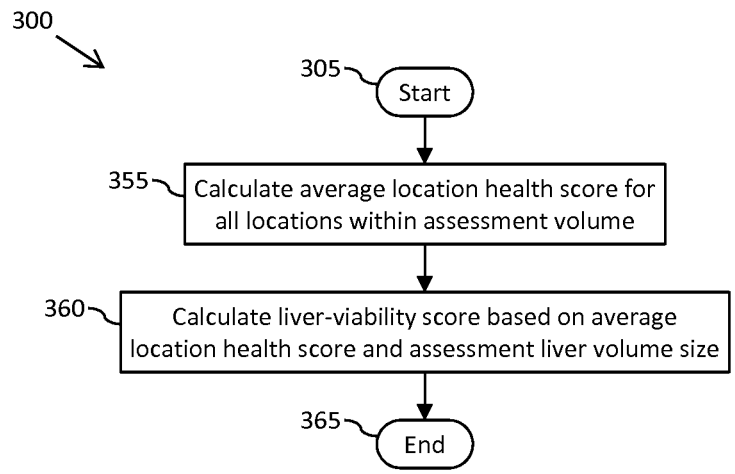
FIG. 3 illustrates a simplified flowchart of an example of a method of calculating an organ-viability measure when the volumetric map of organ health comprises a health score representative of pathologies present within each location of the organ.

As described above, in some example embodiments the volumetric map of organ health may alternatively comprise a health score representative of pathologies present within each location of the organ. FIG. 3 illustrates a simplified flowchart 300 of an example of a method of calculating an organ-viability measure when the volumetric map of organ health comprises a health score representative of pathologies present within each location of the organ. The method of FIG. 3 starts at 310 and moves on to 355 where an average location health score for all locations within the assessment volume is calculated based on the health scores for those locations within the volumetric map of organ health. The organ-viability score for the assessment volume is then calculated at 360 based on the average location health score and the assessment organ volume size, for example the absolute size of the assessment organ volume or a relative size assessment organ volume (e.g. as a percentage or ratio of the full organ volume). The method then ends at 365.

In accordance with some embodiments, it is contemplated that the step of obtaining a volumetric map of organ health may comprise generating the volumetric map of organ health based on received data indicating the presence of pathologies within locations of at least a part of the organ. For example, the severity of fibrotic or cirrhotic disease in an organ can in certain situations be assessed using elastography-based techniques. These techniques use ultrasound or magnetic resonance imaging (MRI) based methods to measure organ stiffness, a surrogate for fibrotic or cirrhotic disease. Such elastographic techniques have demonstrated value in identifying advanced organ disease. Furthermore, hepatic steatosis can be determined by non-invasive imaging techniques, with MRI being the most accurate. The Applicant's LiverMultiScan (LMS) technology, an MRI-based technology that has gained FDA 510(k) clearance and CE marking to aid clinicians in the diagnosis of early liver disease, uses technology to measure and correct MRI-derived T1 maps of the liver for the presence of hepatic iron, a common co-morbidity in patients with chronic liver disease. In addition to corrected T1 mapping, the Applicant's LMS technology also quantifies hepatic steatosis (fat) and haemosiderosis (iron) using state of the art MRI acquisition and processing techniques. Accordingly, data indicating the presence of pathologies within locations within a liver may be obtained by way of such MRI-based technology.

Figure 4:
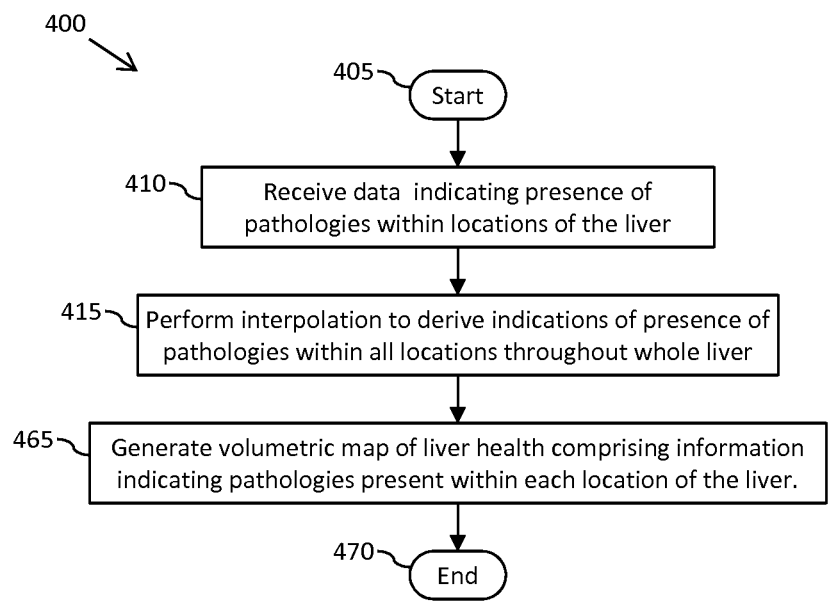
FIG. 4 illustrates a simplified flowchart of an example of a method of generating a volumetric map of organ health comprising information defining an indication of pathologies present within each location of the organ.

FIG. 4 illustrates a simplified flowchart 400 of an example of a method of generating a volumetric map of organ health. The method starts at 405 and moves on to 410 where data indicating the presence of pathologies within locations of at least a part of the organ is received. For example, such information may identify pathologies detected within individual voxels of one or more MRI scan data sets, and said voxels may thus establish at least an initial set of locations for which the presence of pathologies are indicated in the resulting volumetric map of organ health. It is contemplated that such data may relate to only portions of the organ, and not the organ as a whole. Accordingly, in the illustrated example interpolation of the received data is performed at 415 to derive data indicating of the presence of pathologies within locations throughout the whole organ. In the example illustrated in FIG. 4, a volumetric map of organ health is then generated at 465 comprising information defining an indication of pathologies present within each location of the organ. The method then ends at 470.

Figure 5:
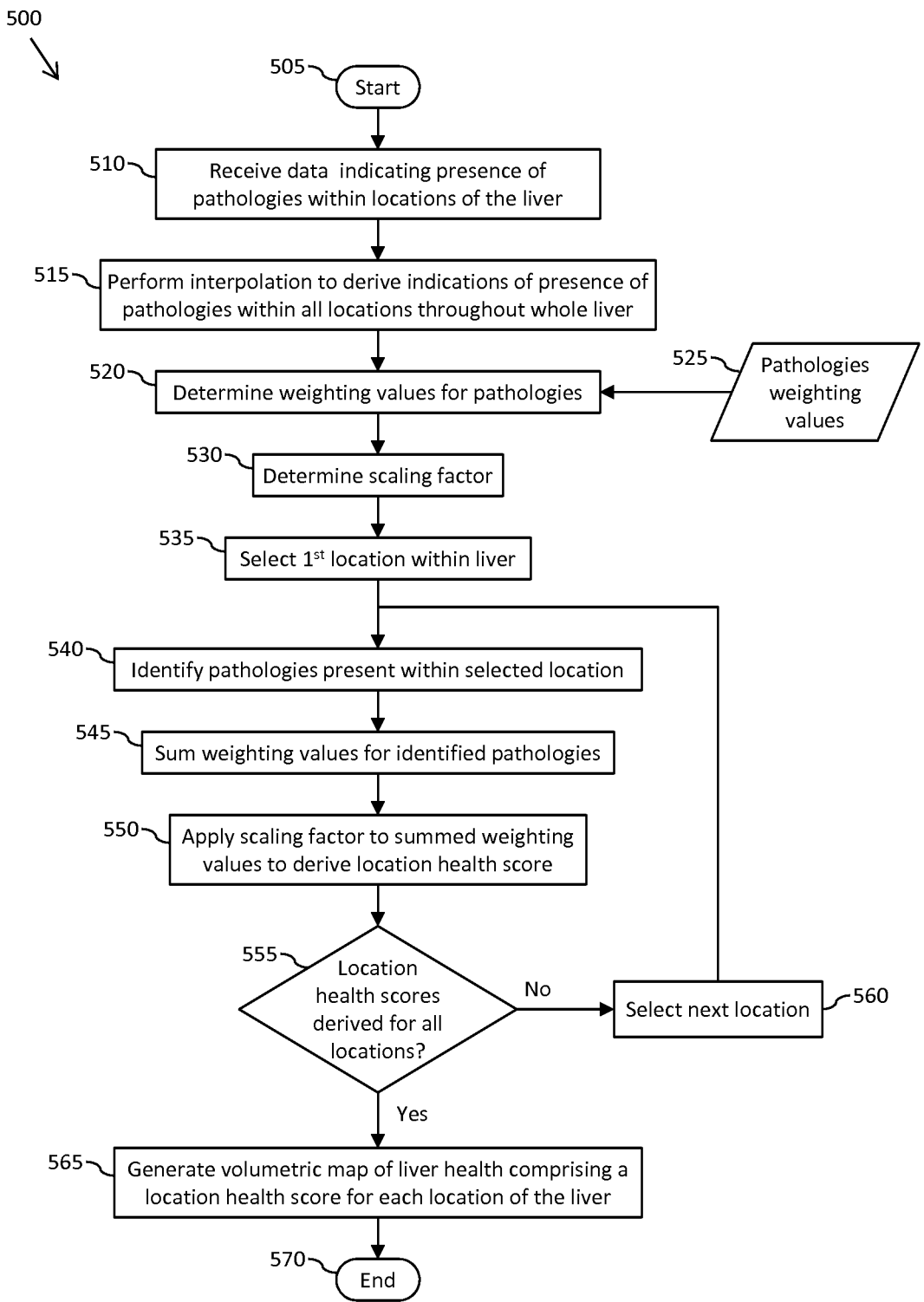
FIG. 5 illustrates a simplified flowchart of an example of a method of generating a volumetric map of organ health comprising a health score representative of pathologies present within each location of the organ.

FIG. 5 illustrates a simplified flowchart 500 of an alternative example of a method of generating a volumetric map of organ health. The method starts at 505 and moves on to 510 where data indicating the presence of pathologies within locations of at least a part of the organ is received. In the illustrated example interpolation of the received data is performed at 515 to derive data indicating the presence of pathologies within locations, or the distribution of pathologies, throughout the whole organ. In the example illustrated in FIG. 5, the method then moves on to 520 where weighting values for pathologies are determined. For example, such pathologies weighting values 525 may be predefined and retrieved from a data storage device. Additionally, alternatively, such pathologies weighting values 525 may be manually entered by a user. In the illustrated example, a scaling factor for the weighting values is then determined at 530. Such a scaling factor may be determined by summing the weighting values and dividing a top-end range value (e.g. 1) by the summed value. A first location within the assessment volume is then selected at 535.

Pathologies present within the selected location are identified at 540 based on the (interpolated) data for that location. The weighted values for the pathologies identified as being present within the selected location are summed at 545. In the illustrated example, the scaling factor determined at 530 is then applied to the summed weighting values at 550 to derive a location health score. It is then determined whether location health scores have been derived for all locations within the organ 555. If it is determined that location health scores have not been derived for all locations within the organ, the next location is selected at 560 and the method loops back to 540.

When it is determined that location health scores have been derived for all locations within the assessment volume at 555, the method moves on to 565 where a volumetric map of organ health is then generated at 465 comprising a health score representative of pathologies present within each location of the organ. The method then ends at 570.

Advantageously, embodiments of the present invention enable medical imaging, such as MRI imaging, to be used to provide a non-invasive, pre-intervention quantitative volumetric assessment of post-intervention organ health, helping doctors personalise their treatment plans to individual patients. In particular, medical imaging may be used to generate a volumetric map of organ health. A user (e.g. a clinician) is then able to provide input to define an assessment organ volume representative of a planned post-intervention organ volume (e.g. an anticipated functioning organ volume remaining following resectional surgery or non-resectional interventions). The volumetric map of organ health may then be used to provide a quantitative volumetric assessment of post-intervention organ health for the planned post-intervention organ volume by way of the organ-viability measure. Thus, quantitative pre-operative information on organ health may be provided to, for example, surgeons and interventional radiologists, enabling them to improve surgical/intervention outcomes and to reduce post-surgical morbidity and cost. In particular, such an assessment is achieved in a non-invasive manner, and enables surgery and/or interventions to be tailored to the individual patient based on the overall health of the patient's organ.

Although example embodiments have been described in relation to providing pre-intervention quantitative volumetric assessment of post-intervention organ health, it is contemplated that the present invention may equally be implemented post-intervention to provide a post-intervention quantitative volumetric assessment of organ-health. Such a post-intervention assessment may be beneficial when, for example, a planned intervention has had to be dynamically adapted mid-intervention due to unforeseen circumstances. Accordingly, such a post-intervention assessment enables a surgeon or interventional radiologist to assess the post-intervention organ health following such an un-planned intervention.

Whilst references to a liver have been made in relation to the above described method of providing a quantitative volumetric assessment of organ health, it is to be understood that the present invention is not limited to being implemented in relation to providing a quantitative volumetric assessment of liver health, and it is contemplated that the present invention may be directed to providing a quantitative volumetric assessment of the health of other organs such as, for example, pancreases, kidneys, etc.

Figure 6:
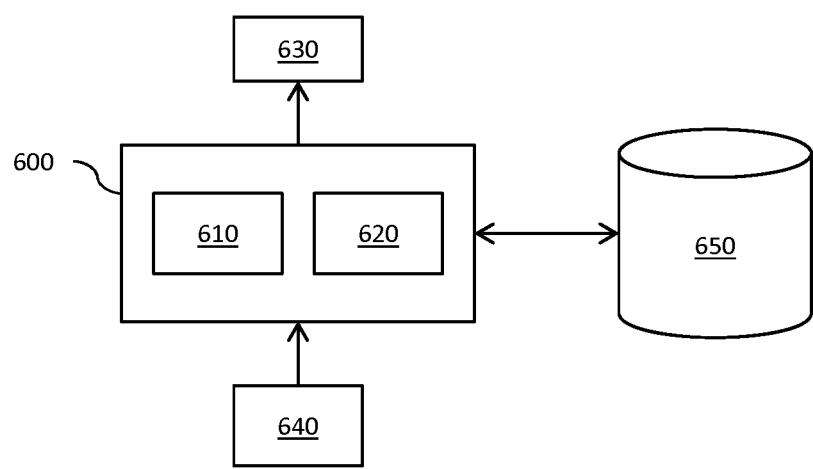
FIG. 6 illustrates a simplified block diagram of an example of apparatus that may be adapted in accordance with examples of the present invention for providing a quantitative volumetric assessment of organ health.

FIG. 6 illustrates a simplified block diagram of an example of apparatus 600 that may be adapted in accordance with examples of the present invention for providing a quantitative volumetric assessment of organ health. The apparatus 600 comprises one or more processing components 610 arranged to perform various processing functions to implement a method of providing a quantitative volumetric assessment of organ health, for example in accordance with one or more of the methods illustrated in FIGS. 1 to 5 and as hereinbefore described. In some example embodiments, one or more of the processing components 610 may comprise one or more programmable components, for example one or more processor cores, arranged to execute computer program code for performing one or more of the steps of such a method. Additionally/alternatively, at least one of the processing components may comprise a hardware processing component arranged to perform one or more of the steps of such a method, such as an application specific integrated circuit (ASIC) device or hardware accelerator module comprising hardware circuity arranged to perform predefined processing of data provided thereto.

The apparatus 600 further comprises one or more memory elements 620. The memory element(s) 620 may consist of one or more non-transitory computer program products such as, for example, a hard disk, an optical storage device such as a CD-ROM device, a magnetic storage device, a Read Only Memory, ROM, a Programmable Read Only Memory, PROM, an Erasable Programmable Read Only Memory, EPROM, an Electrically Erasable Programmable Read Only Memory, EEPROM, and a Flash memory, etc. The memory element 620 may additionally/alternatively comprise one or more volatile memory elements such as, for example, Random Access Memory (RAM), cache memory, etc.

For simplicity and ease of understanding, a single processing device 610 and a single memory element 620 will hereinafter be referred to. However, it will be appreciated that such references to a single processing device 610 or a single memory element 620 are intended to encompass multiple processing devices 610 and multiple memory elements 620 respectively.

The memory element 620 may have stored therein executable computer program code to be executed by the processing device 610. The memory element 620 may further have stored therein data to be accessed and/or processed by the processing device 610 when executing computer program code.

The apparatus 600 illustrated in FIG. 6 further comprises one or more output devices, indicated generally at 630. Such output devices may comprise, by way of example, a display device, a printer device, a network interface device, etc. The apparatus 600 illustrated in FIG. 6 further comprises one or more user input devices, indicated generally at 640. Such input devices may include, by way of example, a keyboard, a keypad, a mouse, a touchscreen, etc.

In accordance with some examples of the present invention, the processing device 610 is arranged to obtaining a volumetric map of organ health comprising information defining a state of tissue health across at least part of an organ, receiving input from a user defining at least one organ section, determining an assessment organ volume based at least partly on the at least one defined organ section, calculating an organ-viability measure for the assessment organ volume based at least partly on information within the volumetric map defining the state of tissue health across the organ volume, and outputting an indication of the organ-viability measure.

Figure 7:
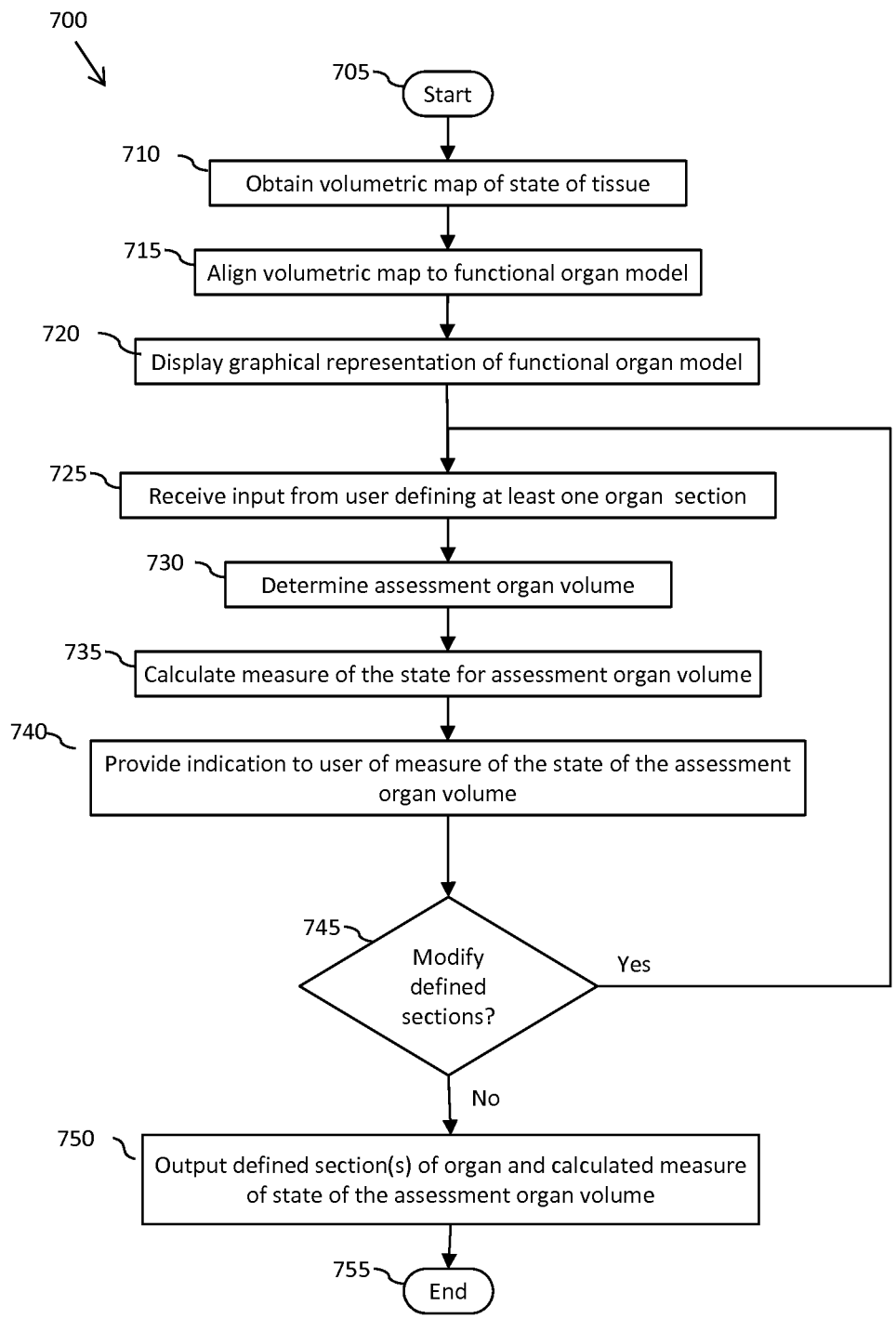
FIG. 7 illustrates a simplified flowchart of an example of a method of providing a quantitative volumetric map of an organ.

FIG. 7 illustrates a simplified flowchart of an example of a method of providing a quantitative volumetric map of an organ. The method 700 of FIG. 7 illustrates the method of the second aspect of the invention, which was also discussed at the end of the description of FIG. 1 above.

In this case, step 710 comprises obtaining a volumetric map of an organ, the volumetric map comprising information defining a state of tissue across at least part of the organ. At step 715, the volumetric map is aligned to a functional organ model. In the method of FIG. 7, the organ may be a liver but could also be another organ. At step 720, a graphical representation of the functional organ model is displayed.

The method further comprises receiving an input from the user defining at least one organ section, as described at step 725. At step 730, an assessment organ volume is determined, based at least partly on the at least one defined organ section. At step 735, the method comprises calculating a measure of the state of the assessment organ volume, based at least partly on information within the volumetric map that is input at step 710 defining the state of the tissue across the organ volume.

At step 740, an indication is provided to a user of the measure of the state of the assessment organ volume. At 745, a user may modify the defined sections, in which case the method returns to step 725. If no modification to the sections is to be made, then the method proceeds to step 750. At step 750, an indication of the measure of the state of the assessment organ volume is provided as an output.

As described above, the invention may also be implemented in a computer program for running on a computer system, at least including code portions for performing steps of a method according to the invention when run on a programmable apparatus, such as a computer system or enabling a programmable apparatus to perform functions of a device or system according to the invention. An ASIC or other processor, for example, may run a program to implement any part of the invention.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system.

The computer program may be stored internally on a tangible and non-transitory computer readable storage medium or transmitted to the computer system via a computer readable transmission medium. All or some of the computer program may be provided on computer readable media permanently, removably or remotely coupled to an information processing system. The tangible and non-transitory computer readable media may include, for example and without limitation, any number of the following: magnetic storage media including disk and tape storage media; optical storage media such as compact disk media (e.g., CD-ROM, CD-R, etc.) and digital video disk storage media; non-volatile memory storage media including semiconductor-based memory units such as FLASH memory, EEPROM, EPROM, ROM; ferromagnetic digital memories; MRAM; volatile storage media including registers, buffers or caches, main memory, RAM, etc.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the scope of the invention as set forth in the appended claims and that the claims are not limited to the specific examples described above.

Those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, the examples, or portions thereof, may implemented as soft or code representations of physical circuitry or of logical representations convertible into physical circuitry, such as in a hardware description language of any appropriate type.

Also, the invention is not limited to being implemented in computer program code, and may equally be implemented, at least partly, by way of physical devices or units implemented in non-programmable hardware, as well as in programmable devices or units able to perform the desired device functions by operating in accordance with suitable program code, such as mainframes, minicomputers, servers, workstations, personal computers, notepads, personal digital assistants, electronic games, automotive and other embedded systems, cell phones and various other wireless devices, commonly denoted in this application as 'computer systems'.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms 'a' or 'an,' as used herein, are defined as one or more than one. Also, the use of introductory phrases such as 'at least one' and 'one or more' in the claims should not be construed to imply that the introduction of another claim element by the indefinite articles 'a' or 'an' limits any particular claim containing such introduced claim element to inventions containing only one such element, even when the same claim includes the introductory phrases 'one or more' or 'at least one' and indefinite articles such as 'a' or 'an.' The same holds true for the use of definite articles. Unless stated otherwise, terms such as 'first' and 'second' are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

We claim:

1. A method of providing a quantitative volumetric assessment of organ health, the method comprising:
   obtaining a volumetric map of organ health comprising information defining a state of tissue health across at least part of an organ and aligning the volumetric model of organ health to a functional model;

receiving an input from a user defining at least one organ section, said section relating to a part of a functional section defined by a functional organ model;

determining an assessment organ volume, based at least partly on the at least one defined functional organ model;

calculating an organ-viability measure for the assessment organ volume, based at least partly on information within the volumetric map defining the state of tissue health across the organ volume; and outputting an indication of the organ-viability measure.

2. The method of claim 1, wherein the method further comprises displaying a graphical representation of the functional organ model to the user, and receiving the input from the user defining the at least one organ section in relation to the displayed graphical representation of the function organ model.

3. The method of claim 1, wherein the functional organ model is based on the Couinaud classification of organ anatomy.

4. The method of claim 1, wherein the volumetric map of organ health comprises information defining a state of tissue health for each of a plurality of locations throughout the at least part of the organ, said information comprising at least one of:

an indication of pathologies present within the respective location of the organ; and a health score representative of pathologies present within the respective location of the organ.

5. The method of claim 1, wherein the step of calculating the organ-viability measure for the assessment organ volume comprises:

calculating an average location health score for all locations within the assessment volume based on information within the volumetric map defining the state of tissue health across the organ volume; and calculating the organ-viability measure for the assessment organ volume based on the average location health score and the assessment organ volume size.

6. The method of claim 5, wherein the average location health score for all locations within the assessment volume comprises:

identifying pathologies present within each location based on information within the volumetric map defining the state of tissue health across the organ volume;

for each location summing weighting values for pathologies identified within that location; and calculating the average location health score based on the summed weighting values for all locations within the assessment volume.

7. The method of claim 1, wherein the assessment organ volume comprises one of:

the at least one defined organ section; and the remaining organ volume excluding the at least one defined organ section.

8. The method of claim 1, wherein the method comprises:

generating the volumetric map of organ health based on received data indicating the presence of pathologies within locations of at least a part of the organ.

9. The method of claim 8, wherein the method further comprises:

performing interpolation of the received data indicating the presence of pathologies within locations of the organ to derive indications of the presence of pathologies within locations throughout the whole organ, and generating the volumetric map of organ health based on the derived indications of the presence of pathologies within locations throughout the whole organ.

10. The method of claim 8, wherein the step of generating the volumetric map of organ health comprises:

identifying pathologies present within individual locations of the organ;

for each of said locations summing weighting values for pathologies identified within that location to derive a location health score; and generating the volumetric map of organ health comprising the derived location health scores.

11. The method of claim 1, wherein outputting the indication of the organ-viability measure comprises one or more of:

displaying the organ-viability measure to a user;

storing the organ-viability measure in at least one data storage device; and transmitting the organ-viability measure to at least one external device.

12. The method of claim 1, wherein the at least one organ section is one of a set of pre-defined functional sections of the organ, based on a segmental anatomy of the organ.

13. The method of claim 12, wherein the set of pre-defined organ sections are sections of the Couinaud classification system.

14. The method of claim 12, wherein a selection of at least one pre-defined organ section is an interactive process, whereby the user is able to select and/or unselect different segments and combinations of segments.

15. The method of claim 12, wherein a received input defines one or more sections, at least one of the sections being only part of a function section, thereby excluding at least another part of the function section.

16. The method of claim 1, wherein the input volumetric map of organ health is a corrected MRI-derived T1 map of the liver.

17. A method of providing a quantitative volumetric map of an organ, the method comprising:

obtaining a volumetric map of an organ, the volumetric map comprising information defining a state of tissue health across at least part of an organ;

receiving an input from a user defining at least one organ section said section relating to a part of a functional section defined by a functional organ model;

determining an assessment organ volume, based at least partly on the at least one defined organ section;

calculating a measure of the state of the assessment organ volume, based at least partly on information within the input volumetric map defining the state of the tissue health across the organ volume; and outputting an indication of the measure of the state of the assessment organ volume.

18. An apparatus for providing a quantitative volumetric assessment of organ health or a quantitative volumetric map of an organ, the apparatus comprising:

at least one processing component and at least one memory element: wherein the at least one processing component is arranged to perform the steps of:

obtaining a volumetric map of organ health comprising information defining a state of tissue health across at least part of an organ;

receiving an input defining at least one organ section;

determining an assessment organ volume, based at least partly on the at least one defined organ section;

calculating an organ-viability measure for the assessment organ volume, based at least partly on information within the volumetric map defining the state of tissue health across the organ volume; and outputting an indication of the organ-viability measure.

19. The apparatus of claim 18, wherein the apparatus further comprises at least one output component for outputting the indication of the organ-viability measure, the at least one output component comprising at least one of:
- a display device for displaying the organ-viability measure to a user;
- a data storage device for storing the organ-viability measure; and
- an interface component for transmitting the organ-viability measure to at least one external device.

* * * * *